United States Patent [19]
Toyoshima et al.

[11] Patent Number: 4,670,584
[45] Date of Patent: Jun. 2, 1987

[54] PHARMACEUTICAL COMPOSITION HAVING AN EXCELLENT ABSORPTION PROPERTY

[75] Inventors: Shigeshi Toyoshima, Tama; Yoshiko Seto, Funabashi; Koji Fukushima, Tama; Izumi Kumashiro, Tokohama, all of Japan

[73] Assignee: Ajinomoto Company Incorporated, Tokyo, Japan

[21] Appl. No.: 873,852

[22] Filed: Jun. 10, 1986

Related U.S. Application Data

[63] Continuation of Ser. No. 656,471, Oct. 1, 1984, abandoned.

[51] Int. Cl.$^4$ ............................................ C07C 101/08
[52] U.S. Cl. .................................... 562/449; 562/443; 562/445; 562/450
[58] Field of Search ............... 562/443, 449, 445, 450; 514/546

[56] References Cited

U.S. PATENT DOCUMENTS 4,380,646  4/1983  Franzmann ........................ 562/445

FOREIGN PATENT DOCUMENTS 2553689  10/1976  Fed. Rep. of Germany ...... 562/445
49-4210   1/1974   Japan .................................. 562/445

OTHER PUBLICATIONS

Vidugiriene et al, Chem. Abst., vol. 77, #152539k (1972).
Takeuchi et al, Chem. Abst., vol. 95, #144605k (1981).
Takeuchi et al, Chem. Abst., vol 99, #192,209p (1983).
Van Sumere et al, J. of Chromatography, vol. 234, pp. 141-155, (1982).

Primary Examiner—James H. Reamer
Attorney, Agent, or Firm—Oblon, Fisher, Spivak, McClelland & Maier

[57] ABSTRACT

An absorption promoter is disclosed which interacts with hydrophobic amino acid residues of polypeptide derivative medications and substantially increases the absorption of that medication administered orally or rectally. The promoter and medication can be compounded into unit dosages in capsule, tablet, or suppository form, or combined into elixir solutions, suspensions, etc. The absorption promoters are phenylalanine derivatives which may be prepared through conventional N-acylation techniques.

1 Claim, No Drawings

PHARMACEUTICAL COMPOSITION HAVING AN EXCELLENT ABSORPTION PROPERTY

This application is a continuation of application Ser. No. 656,471, filed Oct. 1, 1984, now abandoned.

BACKGROUND OF THE INVENTION

Field of the Invention

The present invention relates to a novel pharmaceutical composition or preparation comprising at least a phenylalanine derivative as an excellent absorption promoter, and a medicine. Thereby, the absorption of the medicine can be remarkably improved in oral or rectal administration.

SUMMARY OF THE INVENTION

The phenylalanine derivative is a compound represented by the general formula (I):

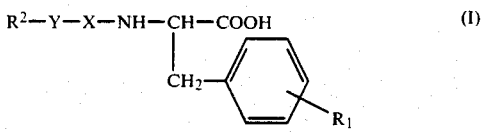

wherein $R^1$ is a hydrogen atom, a fluorine atom, a nitro group, a hydroxyl group or a hydroxyl group protected by an esterifying group; X is CO or $SO_2$; —Y— is a straight bond, a lower alkylene group, a substituted or unsubstituted vinylene group, or a group having the formula —$CH_2$—O— or —O—$CH_2$; $R^2$ is a substituted or unsubstituted phenyl or naphthyl group or $R^2$—Y—CO— is an N-benzyloxycarbonylphenylalanyl, N-benzyloxycarbonyl-4-fluorophenylalanyl, or N-(m-methoxycinnamoyl)phenylalanyl group; or a non-toxic salt thereof.

An example of the hydroxyl group protected by an esterifying group is a benzyloxycarbonyl group. Examples of group $R^2$ include phenyl and naphthyl groups which may have a halogen atom such as chlorine or fluorine atom, a nitro group, a lower alkyl group such as methyl, trifluoromethyl, or a lower alkyloxy group such as methoxy as a substituent.

The compounds having formula (I) are of particular value in that they can be used as a medicine absorption promoter. Phenylalanine per se, or N-acetylphenylalanine or lower alkyl esters or amides of the acids of formula (I) are not useful as absorption promoters. The compounds of formula (I) have asymmetric carbon atoms and may take on a D-form, L-form or a DL-form depending upon the specific combination of substituents. The phenylalanine derivatives used for the present invention are known or novel, and can be prepared by conventional N-acylation techniques.

The phenylalanine derivatives of the present invention may be in a form of a salt, such as a metal salt, for example, sodium, potassium, lithium, and calcium salts, and a salt with an organic base which is pharmaceutically acceptable. As the organic base, there can be adopted amines such as ammonia (ammonium salt), dicyclohexylamine, and N-methyl-D-glucamine, and basic amino acids such as lysine and arginine.

The phenylalanine derivative in the present invention is administered orally or rectally together with the medicine. In the case of insulin, it not only only promotes the absorption of insulin but also inhibits the degradation of insulin in the presence of trypsin and chymotrypsin.

As oral or rectal administration of insulin for the treatment of diabetes mellitus has not been clinically established yet, the development of an insulin-absorption promoter that permits extended and convenient use for humans is needed.

DETAILED DESCRIPTION OF THE INVENTION

The medicine with which the derivatives of the invention may be used is, for example, a polypeptide, or derivatives, or an analogue of such compounds, which has two or more hydrophobic amino acid residues being close to each other or in a cluster at one or more regions so that the said residues interact noncovalently with the hydrophobic portions of the adjuvant. Included in this group are, a soluble globular protein having a cluster or clusters of hydrophobic amino acid residues on the surface such as insulin, insulin-like growth factor I, insulin-like growth factor II, pancreatic polypeptide, a cyclic peptide having two or more hydrophobic amino acid residues being close to each other or in a cluster such as cyclic peptide hormones, and the preferred conformation, which is induced by the presence of the adjuvant from a random coil or other forms of the polypeptide and its derivatives and their analogues, and has two or more hydrophobic amino acid residues being close to each other or in a cluster at one or more regions such as peptide hormones and effectors.

The absorption promoter of the present invention (the phenylalanine derivative) may be employed in the range of from 0.1–2,000 mg preferably 0.2–500 mg to 25 U of the medicine, for example, insulin.

The absorption promoter may be administered in composition form with the medicine.

Regarding the composition form, the phenylalanine derivative can be used by formulating it into preparations such as tablets, capsules, elixirs solutions, suspensions, etc.

The phenylalanine derivative and the medicine such as insulin can be administered to a subject necessitating such treatment (humans) in a dosage range of 0.1–1,000 mg per subject generally several times a day, that is, in a total daily dosage of 0.2–2,000 mg. The dosage varies according to the seriousness of disease, the body weight of subjects, and other factors acknowledged by those skilled in the art.

The foregoing typical combinations of drug are formulated into pharmaceutical compositions set forth below. About 0.2–500 mg of the phenylalanine derivative and the medicine such as insulin are blended into unit dosage forms generally acknowledged or required for the pharmaceutical practice together with pharmaceutically acceptable vehicles, carriers, excipients, binders, antiseptics, stabilizers, flavorings, and so forth. The amount of each active substance in these compositions or preparations is adjusted in such a way as to give an appropriate dosage of the prescribed range.

Specific materials which can be incorporated into tablets, capsules, and so forth are as follows: A binder such as traganth, gum arabic, cornstarch, and gelatin; an excipient such as microcrystalline cellulose; a swelling agent such as cornstarch, pregelatinized starch, and arginic acid; a lubricant such as magnesium stearate; a sweetener such as sucrose, lactose and saccharin; a flavoring such as peppermint, an oil from Gaultheria adenothrix Maxim, and cherry. Enteric coating may be favorably used. For example, hydroxyphenylmethylcellulose (8%) aqueous solution as pre-coating agent for undercoat and hydroxypropylmethylcellulose phthalate (10%) and polyacetyne (3%) aqueous solution as coating agent are used. When the unit dosage form of the preparation is a capsule, a liquid carrier such as a fatty oil can further be incorporated in the foregoing type materials. Various other materials can be present as a coating material or in order to vary the physical form of unit dosage forms according to other methods. For example, tablets can be coated with shellac and/or sugar. Syrups or elixirs can contain active compounds, sucrose as a sweetener, methyl- and propylparaben as an antiseptic, a coloring matter, a flavoring such as cherry and an orange flavoring.

Aseptic compositions can be formulated according to the usual practice for preparation of pharmaceutical dosage forms, in which practice an active substance is dissolved or suspended in a vehicle such as water.

A buffer, antiseptic, and an antioxidant can further be incorporated as occasion demands.

EXAMPLES

The examples for preparation of the compounds used for the active ingredient of the present invention will be shown as follows:

Examples for Preparation 1

Production of "S-6",

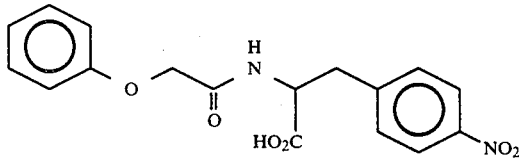

4-Nitro-L-phenylalanine (21 g) was dissolved in 10% NaOH (10 ml), and an ethyl ether solution of phenoxyacetyl chloride (1.7 g) and an aqueous $Na_2CO_3$ solution prepared from $Na_2CO_3$ 2.7 g and water 25 ml were alternately added stepwise thereto while stirring at room temperature over 20 minutes. After that, the mixture was stirred at a room temperature for 3 hours, and then acidified with dilute HCl to precipitate the crystals. The crystals were filtered, washed with water, and re-crystallized from dioxan to obtain N-phenoxyacetyl-4-nitro-L-phenylalanine as needles having melting point: 147° C. (2.4 g).

Calc. C, 59.30%, H, 4.68%, N, 8.14%, Found C, 59.47%, H, 4.51%, N, 8.03%.

Example for Preparation 2

Production of "S-8",

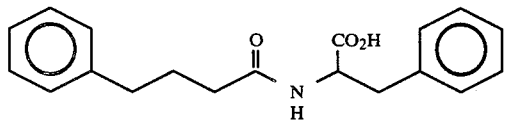

4-phenylbutyric acid (25 g) was dissolved in chloroform (500 ml) and N-hydroxysuccinimide (17.3 g) was added thereto. N,N'-dicyclohexylcarbodiimide (31 g) was added in some portions to the above mixture with ice-cooling while stirring. The mixture was stirred for 1 hour under cooling and then for 7 hours at room temperature. After an addition of glacial acetic acid (10 ml), the mixture was stirred for 1 hour, the insoluble matter was removed by filtration and the filtrate was evaporated to dryness under reduced pressure. The residue was allowed to recrystallize from ethyl acetate to obtain 4-phenylbutyric acid N-hydroxysuccinimide ester (35 g) having melting point: 92° C.

The above mentioned ester (13 g) was dissolved in chloroform (200 ml). This solution was added dropwise to the solution obtained by dissolving L-phenylalanine (16.5 g) and $Na_2CO_3$ (15.9 g) in water (150 ml) while stirring at room temperature. After that, the mixture was stirred for 7 hours and the insoluble matter thus produced was removed by filtration. The filtrate was acidified to pH 1.0 with 6N HCl. The precipitated crystals were filtered, washed with water, and recrystallized from 90% aqueous methanol to obtain N-(4-phenyl-butyroyl)-L-phenylalanine (11.2 g) having melting point: 178° C.

Elementary analysis: Calc. C, 73.28%, H, 6.79%, N, 4.49%, Found C, 73.24%, H, 6.94%, N, 4.46%.

Optical rotation: $[\alpha]_D^{26} = +8.33°$ (C=1, acetone)

In the same manner as above, the following products as listed were obtained:

| Product | Molecular Formula | m.p. (°C.) | Optical rotation |
|---|---|---|---|
| S-24 | $C_{18}H_{16}ClNO_3$ | 155–158 | $[\alpha]_D^{30} - 31.02°$ (C = 1, MeOH) |
| 25 | $C_{18}H_{16}ClNO_3$ | 157–159 | $[\alpha]_D^{30} + 31.20°$ (C = 1, MeOH) |
| 27 | $C_{19}H_{19}NO_3$ | 135–140 | $[\alpha]_D^{25} - 35.89°$ (C = 1, MeOH) |
| 30 | $C_{19}H_{16}F_3NO_3$ | 158–160 | $[\alpha]_D^{20} - 19.10°$ (C = 1, MeOH) |
| 31 | $C_{18}H_{16}FNO_3$ | 145–148 | $[\alpha]_D^{20} - 50.98°$ (C = 1, MeOH) |
| 36 | $C_{19}H_{16}F_3NO_3$ | 157–160 | $[\alpha]_D^{20} + 19.03°$ (C = 1, MeOH) |

Example for Preparation 3

Production of "S-11",

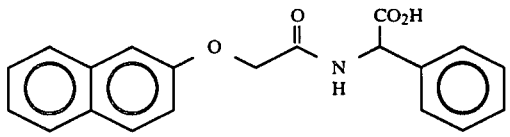

L-Phenylalanine (0.1 mole) was dissolved in 2N-NaOH (50 ml) and ethyl ether (20 ml) was added thereto. To the mixture while stirring vigorously with ice-cooling the desired naphthoxyacetylc chloroform (0.1 mole) and 2N-NaOH (100 ml) in small portions were added. The mixture was stirred for 3 hours at room temperature and washed once with ethyl ether. The aqueous layer was adjusted to pH 2 with 4N-HCl to precipitate crude crystals. The crystals were placed on a filter paper, dried and re-crystallized from ethylacetate-petroleum ether. Compound "S-12" was produced in the same manner as above. The results were obtained as follows:

TABLE 1

| Product | Melting Point (°C.) | $[d]^{20}$ (C = Dl, methanol] | Yield on Purified Crystal |
|---|---|---|---|
| N—[(1-naphthoxy)acetyl]-L-phenylalanine (S-11) | 137–142 | −10.6° | 33 |
| N—[(2-naphthoxy)acetyl[-L-phenylalanine (S-12) | 173–176 | +25.1° | 36 |

Example for Preparation 4

Production of "S-21", Z-Phe$^L$-Phe$^D$

D-Phenylalanine (17.3 g) and NaHCO$_3$ (17.6 g) were added to water (150 ml).

N-Benzyloxycarbonyl-L-phenylalanine N-hydroxysuccinimide ester (27.7 g) was dissolved in tetrahydrofuran (150 ml) and the thus obtained solution was added to the above aqueous solution at room temperature. The mixture was reacted overnight. To the reaction solution, water (200 ml) was added and then the aqueous phase was adjusted to pH 2 with cooled 4N-HCl. The desired product was extracted with ethyl acetate (500 ml). The organic layer was washed with 1N HCl, and saturated aqueous NaCl solution, in order, and dried over anhydrous magnesium sulfate. The solution was evaporated to dryness under reduced pressure. The obtained residue (28.0 g) was re-crystallized from ethyl acetate-n-hexane to obtain the object product (20.3 g, yield: 65%).

In the same manner as above, "S-22", "S-23" and "S-32" were obtained.

| Product | | m.p. (°C.) | Optical Rotation |
|---|---|---|---|
| S-21 | C$_{26}$H$_{26}$N$_2$O$_5$ | 119–125 | $[\alpha]_D^{17} = -34.2°$ (C = 1, EtOH) |
| S-22 | C$_{26}$H$_{25}$FN$_2$O$_5$ | 158–163 | $[\alpha]_D^{23} = +13.9°$ (C = 1, EtOH) |
| S-23 | C$_{26}$H$_{25}$FN$_2$O$_5$ | 133–135 | $[\alpha]_D^{23} = -19.5°$ (C = 1, EtOH) |
| S-32 | C$_{28}$H$_{28}$N$_2$O$_5$ | 189–191 | $[\alpha]_D^{22} = -24.0°$ (C = 1, DMF) |

The present invention is hereunder described in greater detail by reference to examples and laboratory tests, which are given here for illustrative purposes only and are by no means intended to limit the scope of the invention.

Examples and Laboratory Tests

The absorption promoter samples listed in Table 2 were dissolved or suspended in 0.5% CMC-0.05M tris-HCl buffers (pH: 7.8) and the solutions or suspensions were mixed with aqueous insulin solution. Female ICR-CD-1 mice 5 to 7 weeks old were orally administered predetermined amounts of the mixtures. A predetermined duration later, the percent decrease in blood glucose and the degree of elevation of blood insulin as compared with the control group were measured. The results are shown in Table 2. The symbol "Z" in the structural formulas in the table represents a benzyloxycarbonyl group. The upper figures in the columns "effectiveness" represent the percent decrease in blood glucose and the lower parenthesized figures indicate the degree of elevation in blood insulin.

TABLE 2

| Sample No. | Structure | Dose with Insulin 2.5 U/10 g (Body Weight) | (1) Decrease in Blood Glucose (%) (2) Degree of Elevation of Blood Insulin Time (minutes) | |
|---|---|---|---|---|
| | | | 30 | 60 |
| S-1 | naphthyl-CH$_2$-CO-Phe$^L$ | 6.0 mg/10 g | 84.9 (56.4) | 75.4 (60.0) |
| S-2 | O$_2$N-C$_6$H$_4$-O-CH$_2$-CO-NH-CH(CO$_2$H)-CH$_2$-C$_6$H$_4$-NO$_2$ (DL$^-$) | 6.0 mg/10 g | 23.2 (>119) | 60.0 (89.7) |
| S-3 | C$_6$H$_5$-CH=CH-CO-Phe$^L$ | 6.0 mg/10 g | 84.4 (34.2) | 84.3 (68.1) |
| S-4 | Z-HN-CH(CO$_2$H)-CH$_2$-C$_6$H$_4$-O-Z (L$^-$) | 3.0 mg/10 g | 52.7 (6.54) | 31.1 (2.04) |

TABLE 2-continued

| Sample No. | Structure | Dose with Insulin 2.5 U/10 g (Body Weight) | (1) Decrease in Blood Glucose (%) (2) Degree of Elevation of Blood Insulin Time (minutes) 30 | 60 |
|---|---|---|---|---|
| S-5 | C6H5-O-CH2-C(=O)-L-Phe | 12.5 mg/10 g | 57.9 (88.5) | 33.5 (18.0) |
| S-6 | C6H5-O-CH2-C(=O)-NH-CH(CO2H)-CH2-C6H4-NO2 (L-) | 3.1 mg/10 g | 21.5 (20.6) | 44.7 (21.8) |
| S-7 | Z—L-Phe—L-Phe | 3.0 mg/10 g | 70.0 (7.72) | 40.6 (9.35) |
| S-8 | C6H5-(CH2)3-C(=O)-L-Phe | 6.0 mg/10 g | 57.1 (7.31) | 35.6 (9.64) |
| S-9 | C6H5-O-CH2-C(=O)-D-Phe | 3.0 mg/10 g | 37.3 (11.8) | 29.7 (2.67) |
| S-10 | Z—L-Phe—L-Tyr | 6.0 mg/10 g | 61.5 (41.9) | 43.4 (4.85) |
| S-11 | 1-Naphthyl-O-CH2-C(=O)-L-Phe | 6.0 mg/10 g | 54.0 (11.8) | 59.7 (5.07) |
| S-12 | 2-Naphthyl-O-CH2-C(=O)-L-Phe | 6.0 mg/10 g | 50.8 (6.05) | 66.8 (5.62) |
| S-13 | 4-Cl-C6H4-O-CH2-C(=O)-L-Phe | 1.5 mg/10 g | 31.9 (43.4) | 18.5 (9.82) |
| S-14 | C6H5-C(=O)-L-Phe | 6.0 mg/10 g | 35.2 (6.31) | 37.8 (3.31) |
| S-15 | Z—L-Phe | 3.0 mg/10 g | 37.5 (3.43) | 60.7 (2.36) |

TABLE 2-continued
| Sample No. | Structure | Dose with Insulin 2.5 U/10 g (Body Weight) | (1) Decrease in Blood Glucose (%) (2) Degree of Elevation of Blood Insulin Time (minutes) 30 | 60 |
|---|---|---|---|---|
| S-16 | Z—Tyr (L) | 6.0 mg/10 g | 31.0 (50.0) | 27.2 (2.99) |
| S-17 | 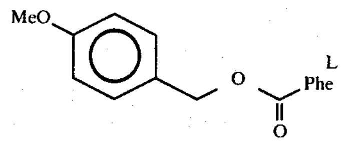 | 3.0 mg/10 g | 64.8 (14.4) | 50.6 (21.2) |
| S-18 | Z—Phe (D) | 6.0 mg/10 g | 52.3 (6.79) | 67.2 (10.6) |
| S-20 | Z—Phe(D)—Phe(L) | 1.5 mg/10 g | 22.4 (2.33) | 32.7 (2.46) |
| S-21 | Z—Phe(L)—Phe(D) | 6.0 mg/10 g | 42.6 (14.9) | 32.7 (5.26) |
| S-22 | 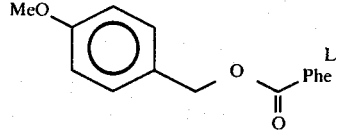 | 3.0 mg/10 g | 63.1 (—) | 51.9 (—) |
| S-23 | 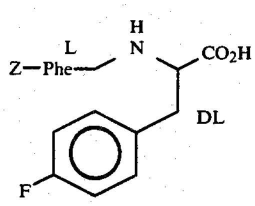 | 3.0 mg/10 g | 67.5 (—) | 39.4 (—) |
| S-24 | 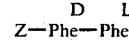 | 1.5 mg/10 g | 37.1 (5.46) | 27.4 (3.04) |
| S-25 | 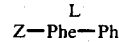 | 1.5 mg/10 g | 34.9 (—) | 29.5 (—) |
| S-27 | 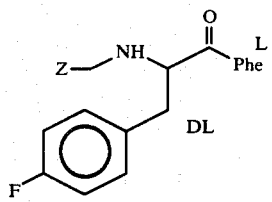 | 1.5 mg/10 g | 61.5 (7.76) | 34.4 (1.0) |
| S-30 | 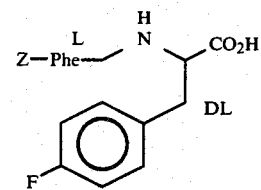 | 3.0 mg/10 g | 48.8 (—) | 44.4 (—) |
| S-31 | 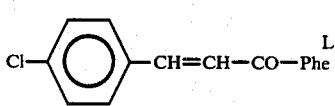 | 3.0 mg/10 g | 33.5 (—) | 72.5 (—) |

TABLE 2-continued

| Sample No. | Structure | Dose with Insulin 2.5 U/10 g (Body Weight) | (1) Decrease in Blood Glucose (%) (2) Degree of Elevation of Blood Insulin Time (minutes) | |
|---|---|---|---|---|
| | | | 30 | 60 |
| S-32 | MeO-C₆H₄-CH=CH-CO-Phe(L)-Phe(L) | 3.0 mg/10 g | — (−) | 23.8 (4.55) |
| S-33 | TS-Phe(L) | 3.0 mg/10 g | 51.6 (18.1) | 21.4 (6.48) |
| S-34 | Ts-Phe(DL) | 6.0 mg/10 g | 27.3 (13.8) | 93.1 (6.52) |
| S-36 | F₃C-C₆H₄-CH=CH-CO-Phe(D) | 3.0 mg/10 g | 52.0 (−) | 49.1 (−) |

To further document the utility of the family of compounds disclosed herein, additional samples were prepared and tested as described below.

PROCESS A

To α-fluorocinnamic acid (5.48 g, 33 mM), thionyl chloride (40 ml) was added, and the thus obtained mixture was stirred at 80° C. under refluxing for 2 hours. After cooling it to a room temperature, the unreacted thionyl chloride was distilled off under reduced pressure to give a syrup-like α-fluorocinnamoyl chloride.

NaOH (1.64 g) was dissolved in water (40 ml) and, in the solution thus obtained D-phenylalanine (6.44 g, 39 mM) was dissolved and acetone (40 ml) was added thereto. The temperature of the solution thus obtained was kept at 10° C. in an ice-water bath.

To the above solution, the acetone solution (90 ml) of α-fluorocinnamoyl chloride as obtained previously and 10% aqueous NaOH solution were alternately added over 30 minutes. In the reaction, the temperature of the solution was adjusted to between 10° and 20° C. and the pH value thereof between 9 and 11. The mixture thus obtained was further stirred for 30 minutes under the same condition. To the solution 6N HCl solution and added to adjust the pH value thereof to between 2 and 3. Hereafter, the solution thus produced is called "SOLUTION A".

Water (320 ml) was added gradually to SOLUTION A under stirring to produce crystals. The crystals were obtained by filtration and washed with water, and recrystallized with an aqueous methanol to give white needle crystals of N-(α-fluorocinnamoyl)-D-phenylalanine (7.73 g, yield 75%).

PROCESS B

Water (450 ml) was added gradually to SOLUTION A as produced from 3-Chlorocinnamic acid (6.02 g, 33 mM) in the same manner as in Experiment 2, to precipitate an oily matter. The oily matter was extracted with ethyl acetate (300 ml). The organic layer was washed with water (300 ml), dried over MgSO₄, and then evaporated to dryness. The solid matter was recrystallized with ethyl acetate-n-hexane to obtain white crystals of N-(3-chlorocinnamoyl)-D-phenylalanine (10.22 g, yield 94%).

In the same manner as the above PROCESS A or PROCESS B, many products were synthesized and listed as follows:

TABLE 3

| Sample No. | Product | PROCESS A or B | Melting point (°C.) | Specific Rotary Power $[\alpha]_D$ | Solvent for recrystallization | Yield (%) |
|---|---|---|---|---|---|---|
| S-37 | 2-Nap—Acr—L-Phe.MeOH | A | 218~219 | $[\alpha]_D^{20} = +34.8°$ (C = 1,b*) | MeOH | 93 |
| S-38 | 2-Nap—Acr—D-Phe.MeOH | A | 219~220 | $[\alpha]_D^{20} = -34.5°$ (C = 1,b) | " | 87 |
| S-39 | 4-Et—Cin—L-Phe | A | 137~138 | $[\alpha]_D^{26} = -34.5°$ (C = 1.5,a*) | MeOH/H₂O | 88 |
| S-40 | 4-Et—Cin—D-Phe | A | 137~138 | $[\alpha]_D^{26} = +35.3°$ (C = 1.5,a) | " | 88 |
| S-41 | 3-Me—Cin—L-Phe | B | 141~142 | $[\alpha]_D^{15} = -28.6°$ (C = 1.7,a) | ACCEt/n-Hexane | 90 |
| S-42 | 3-Me—Cin—D-Phe | B | 140 | $[\alpha]_D^{15} = +29.5°$ (C = 1.7,a) | " | 96 |
| S-43 | 3-Cl—Cin—L-Phe | B | 146 | $[\alpha]_D^{15} = -27.2°$ (C = 1.7,a) | " | 91 |
| S-44 | 3-Cl—Cin—D-Phe | B | 146~147 | $[\alpha]_D^{15} = +26.9°$ (C = 1.6,a) | " | 94 |
| S-45 | 1-Nap—Acr—L-Phe | A | 220~221 | $[\alpha]_D^{20} = +70.6°$ (C = 1.1,b) | Acetone/MeOH/H₂O | 93 |
| S-46 | 1-Nap—Acr—D-Phe | A | 219~221 | $[\alpha]_D^{20} = -69.5°$ (C = 1.8,b) | " | 94 |
| S-47 | 4-Me—Cin—D-Phe | A | 135~136 | $[\alpha]_D^{15} = +34.3°$ (C = 2.0,a) | MeOH/H₂O | 90 |
| S-48 | α-F—Cin—D-Phe | A | 152~153 | $[\alpha]_D^{20} = +46.6°$ (C = 1.2,a) | " | 75 |
| S-49 | α-Cl—Cin—L-Phe.½EtOH | A | 63~65 | $[\alpha]_D^{25} = +3.8$ (C = 1.0 a) | n-Hexane/EtOH/AcOEt | 78 |

TABLE 3-continued

| Sample No. | Product | PROCESS A or B | Melting point (°C.) | Specific Rotary Power $[\alpha]_D$ | Solvent for recrystallization | Yield (%) |
|---|---|---|---|---|---|---|
| S-50 | α-Cl—Cin—D-Phe.½EtOH | A | 65~67 | $[\alpha]_D^{25} = +-4.1\ (C = 1.0\ a)$ | " | 73 |

*a: McOH; b: 0.1N—NaOH 50% aq McOH

Degree of Decrease in Blood Glucose

Each (Administration: 1.5 mg/10 body weight) of the absorption promoters, phenylalanine derivatives as previously listed in the table was dissolved or suspended in 0.01M phosphate buffer (pH 7.5) and the solution or suspension was mixed with aqueous insulin (Administation: 1.25 U/10 g body weight) solution. Male SD rats, 6 weeks old, were intraduodenally administrated with predetermined amounts of the mixtures after being incised abdominally. The incised wounds were sutured quickly. A predetermined duration later, the percent decreases in blood glucose were determined. The results are shown in the following table. In the experiment, four rats a group were used, and the experiment was repeated 2 to 5 times. The mean values of the thus obtained data were described in the table.

TABLE 3

| | Decrease in Blood Glucose (%) | |
|---|---|---|
| Sample No. | 30 minutes | 60 minutes |
| S-37 | 55.3 | 40.2 |
| S-38 | 27.0 | 24.7 |
| S-39 | 56.0 | 32.5 |
| S-40 | 33.9 | 28.1 |
| S-41 | 50.5 | 35.3 |
| S-42 | 48.8 | 40.7 |
| S-43 | 50.9 | 46.9 |
| S-44 | 55.0 | 49.3 |
| S-45 | 41.2 | 35.4 |
| S-46 | 41.6 | 28.8 |
| S-47 | 52.3 | 41.0 |
| S-48 | 73.7 | 72.9 |
| S-49 | 63.2 | 49.1 |
| S-50 | 79.0 | 74.9 |

Some Samples that are suitable for use in the present invention are as follows:

S-1: N-[(1-naphthyl)acetyl]-L-phenylalanine,
S-2: N-[(4-nitrophenoxy)acetyl]-4-nitro-DL-phenylalanine
S-3: N-cinnamoyl-L-phenylalanine,
S-4: N,O-bis-(benzyloxycarbonyl)-L-tyrosine
S-5: N-phenoxyacetyl-L-phenylalanine
S-6: N-phenoxyacetyl-4-nitro-L-phenylalanine
S-7: N-benzyloxycarbonyl-L-phenylalanyl-L-phenylalanine
S-8: N-(4-phenylbutyroyl)-L-phenylalanine
S-9: N-phenoxyacetyl-D-phenylalanine
S-10: N-benzyloxycarbonyl-L-phenylalanyl-L-tyrosine
S-11: N-[(1-naphthoxy)acetyl]-L-phenylalanine
S-12: N-[(2-naphthoxy)acetyl]-L-phenylalanine
S-13: N-[(4-chlorophenoxy)acetyl]-L-phenylalanine
S-14: N-benzoyl-L-phenylalanine
S-15: N-benzyloxycarbonyl-L-phenylalanine
S-16: N-benzyloxycarbonyl-L-tyrosne
S-17: N-(4-methoxybenzyloxycarbonyl)-L-phenylalanine
S-18: N-benzyloxycarbonyl-D-phenylalanine
S-19: N-(4-fluorobenzyloxycarbonyl)-L-phenylalanine
S-20: N-benzyloxycarbonyl-D-phenylalanyl-L-phenylalanine
S-21: N-benzyloxycarbonyl-L-phenylalanyl-D-phenylalanine
S-22: N-benzyloxycarbonyl-4-fluoro-DL-phenylalanyl-L-phenylalanine
S-23: N-benzyloxycarbonyl-L-phenylalanyl-4-fluoro-DL-phenylalanine
S-24: N-(4-chlorocinnamoyl)-L-phenylalanine
S-25: N-(4-chlorocinnamoyl)-D-phenylalanine
S-26: N-(4-fluorocinnamoyl)-L-phenylalanine
S-27: N-(4-methylcinnamoyl)-L-phenylalanine
S-28: N-(4-trifluoromethylcinnamoyl)-L-phenylalanine
S-29: N-(3-methoxycinnamoyl)-L-phenylalanine
S-30: N-(3-trifluoromethylcinnamoyl)-L-phenylalanine
S-31: N-(α-fluorocinnamoyl)-L-phenylalanine
S-32: N-(3-methoxycinnamoyl)-L-phenylalanyl-L-phenylalanine
S-33: N-(4-toluenesulfonyl)-L-phenylalanine
S-34: N-(4-toluenesulfonyl)-DL-phenylalanine
S-35: N-(4-trifluoromethylcinnamoyl)-D-phenylalanine
S-36: N-(3-trifluoromethylcinnamoyl)-D-phenylalanine
S-37: N-(2-Naphthylacryloyl)-L-phenylalanine
S-38: N-(2-Naphthylacryloyl)-D-phenylalanine
S-39: N-(4-ethyl cinnamoyl)-L-phenylalanine
S-40: N-(4-ethyl cinnamoyl)-D-phenylalanine
S-41: N-(3-methyl cinnamoyl)-L-phenylalanine
S-42: N-(3-methyl cinnamoyl)-D-phenylalanine
S-43: N-(3-chlorocinnamoyl)-L-phenylalanine
S-44: N-(3-chlorocinnamoyl)-D-phenylalanine
S-45: N-(1-naphthylacryloyl)-L-phenylalanine
S-46: N-(1-naphthylacryloyl)-D-phenylalanine
S-47: N-(4-methyl cinnamoyl)-D-phenylalanine
S-48: N-(α-fluorocinnamoyl)-D-phenylalanine
S-49: N-(α-Chlorocinnamoyl)-L-phenylalanine ½C₂H₅OH
S-50: N-(α-Chlorocinnamoyl)-D-phenylalanine ½C₂H₅OH Tables 2 and 3 show the effectiveness of the absorption promoter of the present inention when it administered orally, but it should be understood that the same results are obtained by using the absorption promoter as a conventional suppository preparation together with insulin.

As described in the foregoing, the absorption promoter of the present invention is very useful in that it enables clinical insulin therapy by the oral or parenteral (e.g. rectal) route.

Toxicity Studies of Phenylalanine Derivatives with Oral IN Potentiating Activity in Female CD-1(ICR) Mice are as follows:
Chemical Structures of amino acid derivatives LD₅₀ (mg/kg)
N-Phenoxyacetyl-L-phenylalanine >4,000
N-(1-Napthyloxy)acetyl-L-phenylalanine >4,000
N-(2-Naphthyloxy)acetyl-L-phenylalanine >4,000
N-(4-Chlorophenoxy)acetyl-L-phenylalanine >3,500
N-Benzyloxycarbonyl-L-phenylalanine >2,750
N-Benzyloxycarbonyl-D-phenylalanine >4,000
N-p-Methoxybenzyloxycarbonyl-L-phenylalanine 750
N-Benzyloxycarbonyl-L-phenylalanyl-L-phenylalanine >3,000

N-Benzyloxycarbonyl-L-phenylalanyl-L-tyrosine >3,000

N-Cinnamoyl-L-phenylalanine >2,500

Phenylalanine derivatives were suspended in 0.5% CMC.

Example for Tablet

Porcine insulin (0.577 g, 15,000 U, Zn content 0.5%) was dissolved in 0.05N HCl (30 ml) and the thus obtained solution was diluted with distilled water (30 ml).

A compound "S-27" (6 g) was dissolved in 0.1N HaOH (200 ml) and the pH value was adjusted to 7.5 by the addition of 0.1N HCl. The solution was diluted with phosphate buffer (0.02M, pH 7.5) to the volume of 600 ml.

The insulin solution as produced above was added dropwise to the S-27 solution maintained at 20° C. while vigorously stirring, the solution was adjusted to pH 7.5, and immediately was freeze-dried.

There were prepared tablets containing the freeze-dried material (25 mg), with pregelatinzed starch (82 mg), microcrystalline cellulose (82 mg), and magnesium stearate (1 mg). Enteric coating tablets are prepared by the conventional methods using hydroxyphenylmethylcelluloe (8%) aqueous solution as pre-coating agent for undercoat and hydroxypropylmethylcellulose phthalate (10%) and polyacetyne (3%) aqueous solution as coating agent.

Example for Capsule

To glacial acetic acid (250 ml), a compound "S-22' (30 g) was added and dissolved by heating. Porcine insulin (2 g, 52,200 U, Zn content: 0.5%) was added in small portions to the above solution cooled at 20° C. while stirring and dissolved. From the solution the acetic acid was distilled off under reduced pressure at the same temperature.

To the thus obtained solid residue, n-hexane (100 ml) was added and the solid residue was pulverized, then obtained on a filter, and washed with n-hexane. n-Hexane adhered to the powder was evaporated under reduced pressures. The powder was dried under reduced pressures in the presence of soid NaOE.

Dry packed capsules containing 50 mg/capsule of an active ingredient were prepared., the above powder—50 mg Lactose—149 mg Magnesium stearate—1 mg Capsule—200 mg The powder was reduced to a No. 60 powder. Lactose and magnesium stearate were passed through a No. 60 sieve cloth to fall over the foregoing powder and mixed sufficiently with it. The mixture was packed into No. 1 dry gelatin capsules.

What is claimed as new and desired to be secured by Letters Patent of the United States is:

1. An absorption promoter, comprising a phenylalanine derivative, selected from the group consisting of N-(2-Naphthylacryloyl)-L-phenylalanine, N-(2-Naphthyl acryloyl)-D-phenylalanine, N-(4-ethyl cinnamoyl)-L-phenylalanine, N-(4-ethyl cinnamoyl)-D-phenylalanine, N-(3-methyl cinnamoyl)-L-phenylalanine, N-(3-methylcinnamoyl)-D-phenylalanine, N-(3-chlorocinnamoyl)-L-phenylalanine, N-(3-chlorocinnamoyl)-D-phenylalanine, N-(1-Naphthyl acryloyl-L-phenylalanine, N-(1-Naphthyl acryloyl)-D-phenylalanine, N-(4-methoxy cinnamoyl)-D-phenylalanine, N-($\alpha$-fluoro cinnamoyl)-D-phenylalanine and mixtures thereof.

* * * * *

UNITED STATES PATENT AND TRADEMARK OFFICE
CERTIFICATE OF CORRECTION

PATENT NO. : 4,670,584

DATED : June 2, 1987

INVENTOR(S) : Toyoshima, et al.

It is certified that error appears in the above-identified patent and that said Letters Patent is hereby corrected as shown below:

--Priority data was omitted from the Letters Patent.
   It should read:

April 30, 1982 [JP] Japan..........57-73306
   April 14, 1983 [JP] Japan..........58-65999 --

Signed and Sealed this

First Day of September, 1987

*Attest:*

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,670,584

DATED : JUNE 2, 1987

INVENTOR(S) : SHIGESHI TOYOSHIMA ET AL

It is certified that error appears in the above-identified patent and that said Letters Patent is hereby corrected as shown below:

| COL. | LINE |
|---|---|
| 1 | 66, delete second "only", |
| 2 | 38, delete "elixirs" and insert --elixir--, |
| 4 | 29-34, delete "31.02° (C = 1, MeOH) and insert --31.02° U (C = 1, MeOH)--, |
| 4 | 49, delete "naphthoxyacetylc" and insert --naphthoxyacetyl- |
| 4 | 63, delete "methanol]" and insert --methanol)--, |
| 4 | 66, delete "acetyl[" and insert --acetyl]--, |
| 11 | 51, delete "and added" and insert --was added--, |
| 11 | TABLE 3, last line, match parentheses with previous parenthes |
| 13 | 63, delete "tyrosne" and insert --tyrosine--, |
| 14 | 46, delete "inention when it" and insert --invention when it is--, |
| 15 | 25, delete "celluloe" and insert --cellulose--, |
| 15 | 31, delete "S-22' and insert --"S-22"--, |

UNITED STATES PATENT AND TRADEMARK OFFICE
CERTIFICATE OF CORRECTION

PATENT NO. : 4,670,584

DATED : JUNE 2, 1987

INVENTOR(S) : SHIGESHI TOYOSHIMA ET AL

It is certified that error appears in the above-identified patent and that said Letters Patent is hereby corrected as shown below:

| COL. | LINE | |
|---|---|---|
| 16 | 8, | delete "soid" and insert --solid--, |
| 16 | 10, | delete "prepared:," and insert --prepared:-- |

Signed and Sealed this

Seventeenth Day of May, 1988

Attest:

DONALD J. QUIGG

*Attesting Officer*      *Commissioner of Patents and Trademarks*